United States Patent [19]
Ryan

[11] Patent Number: 5,395,348
[45] Date of Patent: Mar. 7, 1995

[54] MEDICAL INTRAVENOUS ADMINISTRATION LINE CONNECTORS

[75] Inventor: Dana W. Ryan, Davie, Fla.

[73] Assignee: Symbiosis Corporation, Miami, Fla.

[21] Appl. No.: 171,918

[22] Filed: Dec. 22, 1993

Related U.S. Application Data

[63] Continuation-in-part of Ser. No. 57,525, May 4, 1993, Pat. No. 5,292,308.

[51] Int. Cl.$^6$ .............................................. A61M 5/00
[52] U.S. Cl. ................................... 604/247; 604/86; 251/149.1
[58] Field of Search ................. 604/82, 83, 86, 87, 604/88, 99, 247, 249, 256, 283, 284; 137/843; 251/149.1, 149.6, 149.7

[56] References Cited

U.S. PATENT DOCUMENTS

| | | | |
|---|---|---|---|
| 3,192,949 | 7/1965 | DeSee | 137/540 |
| 3,799,171 | 3/1974 | Patel | 604/99 |
| 3,806,086 | 4/1974 | Cloyd | 251/149.7 |
| 3,831,629 | 8/1974 | Mackal et al. | 137/525 |
| 4,617,015 | 10/1986 | Foltz | 604/100 |
| 4,681,132 | 7/1987 | Lardner | 137/271 |
| 4,683,916 | 8/1987 | Raines | 604/247 |
| 4,776,369 | 10/1988 | Lardner et al. | 137/515.5 |
| 4,908,018 | 3/1990 | Thomsen | 604/83 |
| 4,915,687 | 4/1990 | Sivert | 604/83 |
| 5,116,021 | 5/1992 | Faust et al. | 251/149.1 |
| 5,163,922 | 11/1992 | McElveen, Jr. et al. | 604/83 |
| 5,215,538 | 6/1993 | Larkin | 604/249 |
| 5,230,706 | 7/1993 | Duquette | 604/83 |
| 5,284,475 | 2/1994 | Mackal | 604/247 |

Primary Examiner—C. Fred Rosenbaum
Assistant Examiner—Chalin Smith
Attorney, Agent, or Firm—David P. Gordon

[57] ABSTRACT

A needleless IV quick-connect/disconnect assembly includes a first cylindrical member having a female luer, a resilient valve member having stem, a sealing surface, and a base, and a second cylindrical member having a fluid coupling extending from one end and an internal valve member support. The cylindrical members are sized so that the first cylindrical member fits snugly inside the second cylindrical member. A pair of radial ramped protrusions extend from the outer surface of the first cylindrical member and a pair of radial openings are provided in the second cylindrical member. In assembly, with the valve member stem in the female luer, the first cylindrical member is inserted into the second cylindrical member until the radial ramped protrusions engage the radial openings and the valve member base is engaged by the valve member support. When assembled, the valve stem extends into the female luer from inside the first cylindrical member and the valve member base biases the sealing ring against an annular ring in the first cylindrical member thereby blocking fluid communication. Coupling a male luer to the female luer of the assembly opens the valve for fluid flow through the assembly, while uncoupling the male luer from the female luer closes the valve and prevents fluid flow therethrough.

18 Claims, 7 Drawing Sheets

MEDICAL INTRAVENOUS ADMINISTRATION LINE CONNECTORS

This application is a continuation-in-part of U.S. Ser. No. 08/057,525 filed, May 4, 1993, now U.S. Pat. No. 5,292,308.

BACKGROUND OF THE INVENTION

1. Field of the Invention

This invention relates to medical IV administration line connectors. More particularly, this invention relates to a needleless medical IV quick-connect/disconnect assembly for attaching and detaching a patient to and from an IV system.

2. State of the Art

Intravenous therapy has a long history of use in supplying patients with medicament, nourishment or fluids. One of the problems associated with intravenous therapy of ambulatory patients is that the patient cannot be easily disconnected from and reconnected to an intravenous administration line for short periods of time. To safely and easily disconnect the patient for even a short period of time requires the assistance of skilled medical personnel. The ambulatory patient is often required to be attached to the intravenous system and must wheel a stand holding the IV liquid supply wherever the patient goes. Being restricted in this manner can cause the patient to forgo activities of short duration that would be beneficial to the patient.

It is often necessary for hospital staff to move patients from location to location within the hospital in order to perform tests and certain medical treatments. It is not necessary or desirable to have the patient hooked up to the intravenous system during some of these activities. Removing a patient from an intravenous system and re-establishing the patient on the system takes a substantial amount of time even for a medical professional skilled in the techniques of intravenous therapy. With hospital costs rising dramatically there is considerable advantage in a connector device that allows the medical staff to be able to quickly and safely connect and disconnect a patient from an intravenous therapy administration line while expending a minimum amount of time in doing so.

The prior art has addressed some of the above stated problems. For example, U.S. Pat. No. 4,511,359 issued to Vaillancourt describes a three-part sterile dialysis connection device for home use. The three parts are a male connector which terminates in a catheter tube; a female connector with a hollow needle secured in place and terminating in a flexible tubing; and a molded septum assembly. Vaillancourt places the molded septum assembly in the receiver end of the female connector. The female connector is then slid over the male connector, thereby pushing the septum assembly into place between the male and female connectors, and into friction fit with the male connector, and also causing the sharpened needle in the female connector to pierce the molded septum assembly. The hollow needle provides a path for fluid flow between the two connector parts. When the male and female connectors are separated, the needle is removed from the self-sealing septum, and the septum assembly remains with and covering the male connector because of its friction fit therewith.

Another three-part home dialysis connection device is described in U.S. Pat. No. 4,810,241 issued to Rogers which provides a sterile connection by mechanical and chemical means. The three parts include two connectors, one attached to an influent tube and the other to the catheter tube, and a cylindrical shaped tube in which there is highly absorbent material saturated with antiseptic. The two connectors in turn connect one to each end of the cylinder. As the end connectors are introduced into the central cylinder connector, they are sterilized by the antiseptic in the cylinder and remain in antiseptic contact during the entire time they are being used for dialysis. A sterile environment is maintained on the catheter tubing side of the IV system only for so long as the catheter side tubing is in the connector cylinder. Care must be taken not to let the disinfectant in the cylinder dry out or evaporate.

A somewhat different solution to the problem was taken by U.S. Pat. No. 4,559,043 issued to Whitehouse, et al. which provides a four-piece assembly including a distal connector, a proximate connector, a septum fitting between and held in place by the distal and proximate connectors, and an adapter with a through bore able to accept a hollow needle, the adapter being used in conjunction with the proximate connector. A hollow needle attached to a standard luer extension T which connects to the adapter is pushed through the adapter needle bore and pierces the septum which is held between the proximate and distal connectors, thereby establishing fluid flow. When the hollow needle attached to the luer T is removed, the septum is sealed, but the needle is exposed, presenting a needlestick hazard.

While these devices of the prior art may be effective for their particular purposes, the requirement for a simple, low-cost, quick-connect/disconnect safety assembly is not filled. The prior art does not show a device which has all of the virtues in a single device of being simple and inexpensive to manufacture, providing standard means such as luer fittings for attachment to other devices, and providing means for shielding the needle after use to prevent accidental needlesticks.

My prior U.S. Pat. No. 5,139,483 (the complete disclosure of which is incorporated herein by reference) teaches an IV quick-connect/disconnect device having molded single piece male and female connectors. The male connector has a male luer-lock on one end, a pair of outwardly extending bayonet knobs on a middle portion and a reduced diameter second end which terminates in a resilient septum. The female connector has a female luer-lock on one end and a receiving cylinder with a pair bayonet cutouts on the other; the luer-lock and the cylinder being separated by a wall through which a hollow needle extends that has been insert molded in the wall. The male and female connectors are mated by sliding the reduced diameter second end of the male connector into the receiving cylinder of the female connector, with the bayonet cutouts of the female connector serving as a track for the extended knobs of the male connector. The connectors are locked into place by bringing the male connector as far forward as possible, and then rotating the male connector such that extending knobs move past a restriction in the cutout and click (lock) into place.

This arrangement overcomes many of the disadvantages of the prior art, but it still has its drawbacks. The female connector is fragile due to the bayonet cutouts and these cutouts form a ragged end surface of the female connector when the connectors are uncoupled. The cut outs can actually catch or snag surgical gloves or other medical equipment. Similarly, the bayonet knobs of the male connector present a ragged surface of the male connector when it is uncoupled from the female connector. Moreover, the bayonet knobs on the male connector sometimes extend slightly beyond the outer surface of the female connector when the connectors are coupled. The extended bayonet knobs of the male connector result in a less than totally smooth surface and this surface can catch, snag and cause tears in surgical gloves, etc. Unfortunately, there is no easy way to avoid this problem because insert molding the needle in the female connector substantially requires that the bayonet cut outs be located on the female connector rather than on the male connector. Indeed, manufacturing considerations have limited the features of these connectors in several ways and the provided features have dictated some inconvenient manufacturing steps. For example, the resilient septum at the second end of the male connector covers a portion of both the inside and the outside wall surface of the second end and is held in place by a thin plastic shrink band. This is not an ideal configuration since the septum and the shrink band are exposed to wear and can be torn. Additionally, the female connectors may carry either an 18 gauge or a 20 gauge needle depending on the type of fluid to be delivered through the connectors. There is presently no simple way of distinguishing the larger gauge needles from the smaller gauge needles without direct comparison.

The parent of this application solves many of the aforementioned disadvantages by providing a suitably molded single piece male connector and a two piece female connector. The male connector has a male luer-lock on one end, one or more inwardly extending bayonet recesses on the surface of a middle section of reduced diameter and a further reduced diameter second end with a cold rolled edge which encloses a resilient molded septum or the like. The first piece of the female connector has a female luer-lock on one end and a first portion of a receiving cylinder on the other, the luer-lock and the first portion of the cylinder being separated by a wall through which a hollow needle extends that has been insert molded or bonded in the wall. The second piece of the female connector is the second portion of the receiving cylinder which is sonically welded to the first piece. The second piece has one or more inwardly extending knobs on its inner surface which are arranged to engage the inwardly extending bayonet recesses of the male connector when the reduced diameter second end of the male connector is placed in the receiving cylinder of the female connector. The pointed end of the hollow needle is located in the second portion of the receiving cylinder. The outside cylindrical surfaces of both the male and female connectors (both before and after mating) are smooth with no projections that can catch or snag other medical equipment.

In using the male and female connectors, an IV administration line with a male luer-lock or luer-slip is inserted into the female luer side of the female connector, while an IV winged needle or catheter device that is connected directly to an extension line or the like which terminates in a female luer-lock or luer-slip is connected with the male luer-lock or luer-slip of the male connector. The male and female connectors are mated by sliding the reduced diameter second end of the male connector into the receiving cylinder of the female connector, with the recesses of the male connector serving as a track for the inwardly extending knobs of the receiving cylinder of the female connector. As the male connector is slid forward, the needle in the female connector pierces the resilient septum which permits the flow of liquid through the septum via the hollow needle. The connectors are locked into place by bringing the male connector as far into the female connector as possible, and then rotating the male and/or female connector such that the knobs on the female connector move past restrictions in the recesses in the male connector and both connectors click (lock) into place. Quick release is obtained by rotating the male and/or female connector in the opposite direction and pulling the male connector straight out relative to the female connector. When the male and female connectors are separated, the needle in the female connector is withdrawn from the self-sealing resilient septum held in the reduced diameter second end of the male connector.

Despite all of the safety features in my earlier patent and in the parent of this application, both devices utilize a needle to pierce a septum. It is currently appreciated that a completely "needleless" IV line connector would offer substantial advantages.

Needleless valves are not unknown in the art of IV administration. U.S. Pat. No. 4,683,916 to Raines, e.g., discloses a normally closed automatic reflux valve for use in the administration of fluids and medicinal liquids in medical environments. The valve includes a two-part body having a male luer lock on one part and a female luer lock on the other part. Both parts also have cylindrical container portions which, when connected, restrain a flexible valve disk. A pointed triangle in one of the cylindrical container portions supports a central area of the disk which in turn is under pressure from a traverse bar mounted in the other cylindrical portion. The pressure between the triangle point and the bar generally is sufficient to restrain the disk against sideways movement. A small plastic plunger having an open cylindrical end and a pair of dependent legs is slidably mounted on top of the disk and extends into the female luer lock. When the tip of a syringe or male luer connector engages the open cylindrical end of the plunger and presses it inward, the disk is flexed against the triangle to open the valve. When the injection device or male luer connector is removed, the resiliency of the disk closes the valve. While Raines' valve has certain advantages, it does not work well. It is easily clogged, especially when glucose solutions are being fed through the valve, and the resiliency of the disk is often insufficient to provide a sealed closure when the male connector is removed.

U.S. Pat. No. 4,908,018 to Thomasen discloses a method and apparatus for injecting fluids into an IV line. Thomasen's device consists of a cylindrical member having a female luer coupling at one end, an annular shoulder, a poppet with an imperforate top engaging the shoulder, and resilient buckling legs biasing the poppet against the shoulder. When a male luer is coupled to the female luer coupling, the poppet is unmoved. When fluid is forced through the coupling, however, the poppet is moved away from the shoulder under the pressure of the fluid. Thomasen's device has several disadvantages. First, it requires that the fluid pressure and the resiliency of the buckling legs be properly matched so that the valve opens and closes as desired. Second, Thomasen's device requires that fluid be injected under pressure before the valve opens. Its use, therefore is limited for injection only, and it cannot be used to withdraw fluids from an IV line.

U.S. Pat. No. 5,230,706 to Duquette discloses a bi-directional valve assembly used in needleless injection or infusion ports. Duquette's valve assembly includes a valve body containing a valve port, a valve plunger having a sealing means, and a spring. The spring urges the valve plunger towards the valve port so that the sealing means seals the valve port. The valve port is disclosed as a female luer-slip and the valve plunger has a stem which enters the luer slip when the valve is sealed. Insertion of a male luer-slip into the valve port engages the stem on the plunger and moves the plunger against the spring to open the valve. Upon removal of the male luer-slip, the spring urges the valve back into the sealing position. Duquette's valve assembly solves many of the problems addressed above. However, it requires at least four parts (valve body, spring, plunger, and valve port) and the assembly of the pieces is difficult since there appears to be no convenient way to connect the valve port to the valve body so that a fluid tight coupling is effected.

U.S. Pat. No. 4,681,132 to Lardner discloses a check valve having a preset cracking pressure. The check valve is assembled from three parts: a valve body, a valve element and a plug. The valve body is sleeve-like having a central axial passageway defining an input and an output and a frustroconical valve seat converging towards the input. The valve element has a stem, a frustroconical seat converging towards the stem, and a resilient annular wall extending from the seat and capable of flexing when pressure is exerted on the stem. The plug is an annular ring which is engagable in a corresponding annular slot formed in the output portion of the valve body. The valve element is inserted into the valve body so that its stem enters the input and its seat abuts the valve body seat. The plug is inserted into the annular slot in the valve body and thereby holds the valve member in the valve body with respective seats in sealing engagement. The valve is opened by applying fluid or mechanical pressure at the input onto the valve element stem. The axial length of the plug determines the amount of compression on the resilient annular wall of the valve element and thereby defines a cracking pressure necessary to open the valve. While the check valve disclosed by Lardner is relatively simple and easy to assemble, it is not readily adapted to use in an IV quick- connect/disconnect assembly. Although the input of Lardner's check valve may serve as a fluid coupling, Lardner does not provide any fluid coupling device at the output of the check valve. Moreover, to do so would add more components to the valve defeating its simplicity and ease of assembly. Furthermore, if Lardner's valve were used in an IV Y-injection port, assembly would be quite difficult in that the insertion of the plug in such a configuration is nearly impossible. In addition, in order to insert the plug in Lardner's check valve, either the output portion of the valve body or the plug itself must be resilient. Therefore, there is never any positive locking of the plug in position and it is always possible that the plug will pop out of the output of the valve body given sufficient force applied at the input of the valve body.

SUMMARY OF THE INVENTION

It is therefore an object of the invention to provide a needleless IV quick-connect/disconnect safety assembly.

A further object of the invention is to provide an IV quick-connect/disconnect assembly with an automatic valve which allows both injection and withdrawal of fluid.

Another object of the invention is to provide an IV quick-connect/disconnect assembly that will reduce the average time it takes medical personnel to establish the IV therapy system servicing a patient.

An additional object of the invention is to provide an IV quick-connect/disconnect assembly that has means at both ends that permit attachment to any type of standard administration lines, extension sets, winged needles, catheters, or other IV medical devices using standard medical attachment means such as luer-locks or luer-slip fittings.

Yet another object of the invention is to provide a normally closed automatic valve having male and female luer connections where the valve is automatically opened by connection of a male luer to the female luer connection of the valve, and where the valve is automatically closed when the male-luer is disconnected from the female luer connection of the valve.

Still another object of the invention is to provide a needleless IV Y-injection port having an integral female luer connector.

Yet another object of the invention is to provide a needleless IV quick-connect/disconnect assembly that is easy to manufacture and assemble and consists of a minimum number of parts.

In accordance with the objects stated above, a needleless IV quick-connect/disconnect assembly is provided and generally comprises: a first cylindrical member having a female luer connector extending from one end and providing a fluid path to the interior of the first cylindrical member, wherein a first seat is formed in the first cylindrical member at the junction of the female luer and the cylindrical opening; a second cylindrical member having a male luer connector extending from one end and providing a fluid path to the interior of the second cylindrical member, wherein a second seat is formed in the second cylindrical member at the junction of the male luer and the cylindrical opening; and a valve member having an integral stem, sealing surface, and resilient base. The outer diameter of the first cylindrical member is slightly smaller than the inner diameter of the second cylindrical member so that it may fit snugly inside the second cylindrical member. At least two radially extending ramped protrusions extend from the outer surface of the first cylindrical member and a corresponding number of radial openings or recesses are provided in the second cylindrical member. The IV quick-connect/disconnect assembly is assembled by placing the valve member into the cylindrical opening of the first cylindrical member so that its stem enters the female luer connector and its sealing surface rests against the first seat. The second cylindrical member is then placed over the first cylindrical member until the radially extending ramped protrusions lockingly engage the radial openings or recesses. In the assembled state, the stem of the resilient valve member extends into the female luer from the inside of the first cylindrical member, and the resilient base of the valve member engages the second seat in the second cylindrical member and biases the sealing surface against the first seat in the first cylindrical member, thereby blocking fluid communication between the female luer and the interior of the first cylindrical member.

According to a preferred embodiment, the integral valve member is a stepped diameter cylinder having a hollow base and a solid stem. The base has a larger diameter than the stem and the step between the base and the stem is preferably frustroconical wherein the sealing surface is formed. The end of the stem is provided with a diametrical slot, and according to one embodiment of the invention which is designed to expedite fluid flow, the slot is provided with chamfered edge sections which lead to longitudinal grooves which run at least partially down the circumference of the stem. To further expedite fluid flow, the top face of the stem may also be provided with a recessed circular area around the slot which funnels fluid into the slot. The surface of the hollow base is provided with a plurality of raised longitudinal ribs. The outer diameter of the valve member base is smaller than the inner diameter of the first and second second cylindrical members so that when the valve member base is supported on the second seat, an annular fluid passage exists between the valve member base and the cylindrical members. The second seat is preferably formed from a plurality of radially arranged vanes which enter the hollow base of the valve member and flare outward from it. Spaces between the vanes provide a fluid passage from the male luer to the annular fluid passage surrounding the valve member base. When a male luer is inserted into the female luer connector, the valve member stem is pressed partially into the first cylindrical member thereby moving the sealing surface away from the first seat and also moving either the diametrical slot or the longitudinal grooves in the valve member stem at least partially inside the first cylindrical member. Fluid is free to pass from the male luer through the diametrical slot (and down the tapered edges and longitudinal grooves if provided) in the valve member stem, out into the first cylindrical member, around the sealing ring, into the annular fluid passage surrounding the valve member base, through the spaces between the radial vanes, and through the male luer connector in the second cylindrical member. When opened, the valve member allows fluid flow in either direction, from the male luer to the female luer or vice versa. When a male luer is withdrawn from the female luer connector, the resilient base of the valve member biases the valve stem back into the female luer connector and thereby moves the sealing surface against the first seat, closing the valve.

According to a second embodiment, the second cylindrical member terminates in a Y-site adapter rather than a male luer lock.

In both of the embodiments, the valve member stem is preferably sized to fit close to the interior wall of the female luer and the exterior diameter of the first cylindrical member is chosen to fit closely within the interior diameter of the second cylindrical member so that a force fitting-is all that is necessary to provide a fluid-tight assembly. The first cylindrical member has a flared inner surface and the ends of the radial vanes of the second seat terminate in a cylinder which engages a flared inner surface of the first cylindrical member to provide a further fluid seal between the first and second cylindrical members.

Additional objects and advantages of the invention will become apparent to those skilled in the art upon reference to the detailed description in conjunction with the accompanying drawings.

BRIEF DESCRIPTION OF THE DRAWINGS

FIG. 14b is an enlarged top view of the alternate valve member of FIG. 14a; and

FIG. 14c is an enlarged broken side elevation view of the alternate valve member of FIG. 14a taken ninety degrees around the valve member from FIG. 14a.

DETAILED DESCRIPTION OF THE PREFERRED EMBODIMENTS

Figure 1:
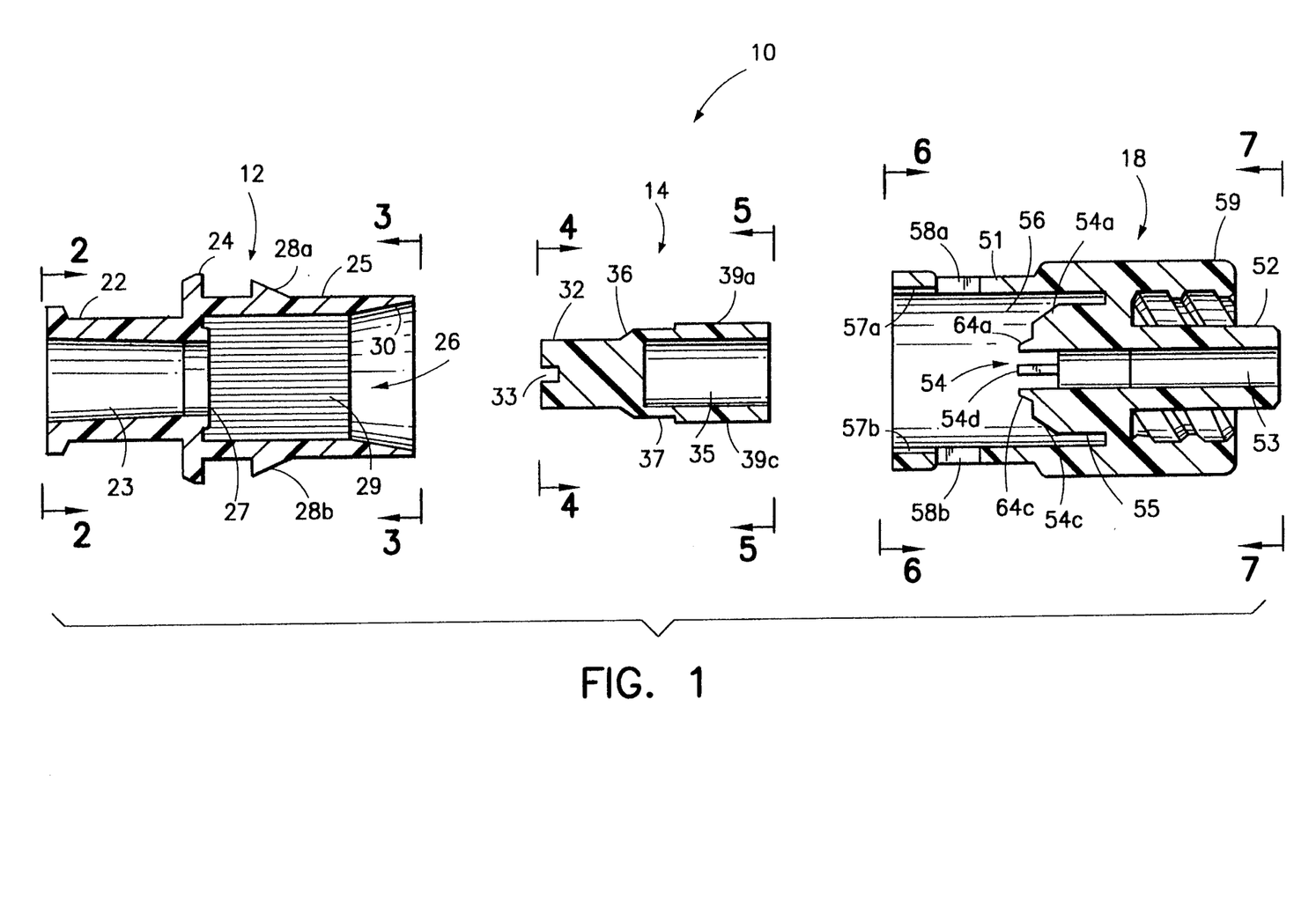
FIG. 1 is an exploded longitudinal cross-sectional view of a first embodiment of the invention.

Turning now to FIG. 1, a first embodiment of the quick-connect/disconnect device 10 for an IV administration line system is shown in an exploded view. The device 10 includes three parts: a first cylindrical member 12, an integral valve member 14, and a second cylindrical member 18. Each part is a single molded piece which is inexpensive and easy to manufacture.

Figure 2:
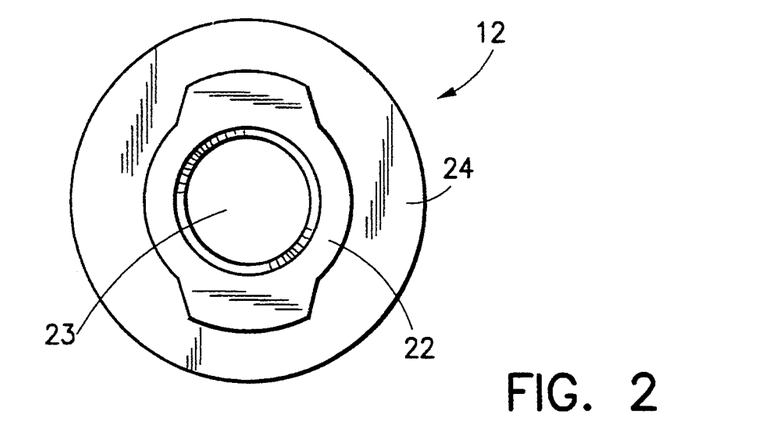
FIG. 2 is an enlarged end view of the female luer connector looking in the direction 2—2 as indicated in FIG. 1.
Figure 3:
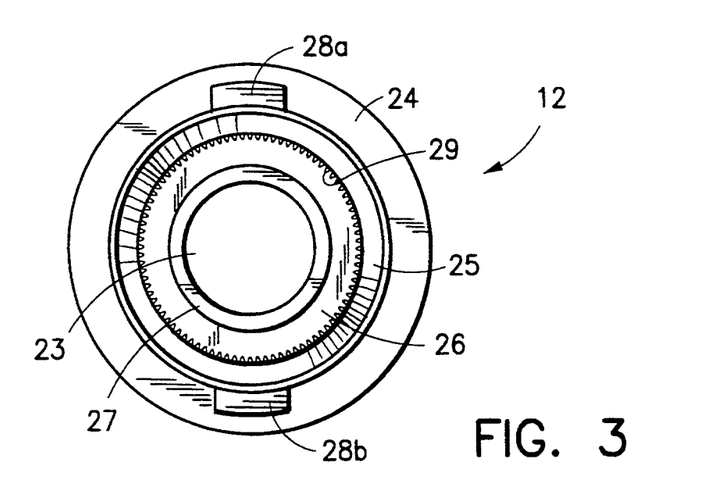
FIG. 3 is an enlarged end view of the first cylindrical member looking in the direction 3—3 as indicated in FIG. 1.

Details of the first cylindrical member 12 can also be seen in FIGS. 2 and 3. As seen in FIGS. 1-3, the first cylindrical member 12 has a female luer connector 22 separated by a flange 24 from a cylinder 25 having a cylindrical interior space 26. Those skilled in the art will appreciate that the female luer 22 provides a fluid path 23 into the interior cylindrical space 26 of the cylinder 25. At the opening from the female luer into the cylindrical space 26, a seat in the form of a slightly protruding annular ring 27 is formed and effectively surrounds the fluid path 23 entry from the female luer 22. The exterior surface of the cylinder 25 is provided with two diametrically opposed radially extending ramped protrusions 28a, 28b. At least a portion of the interior surface of the cylinder 25 is preferably provided with longitudinal ribs 29, which are described in further detail below, and a portion 30 of the interior surface most distant from the female luer 22 is flared as seen best in FIG. 1. The first cylindrical portion is preferably made of molded co-polypropylene polymer such as EXXON Escorene #PD 9074 MED.

Figure 4:
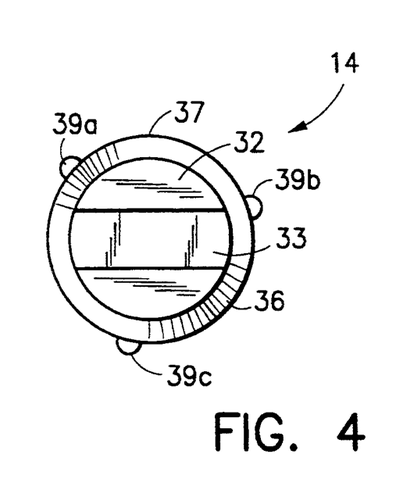
FIG. 4 is an enlarged end view of the valve member looking in the direction 4—4 as indicated in FIG. 1.
Figure 5:
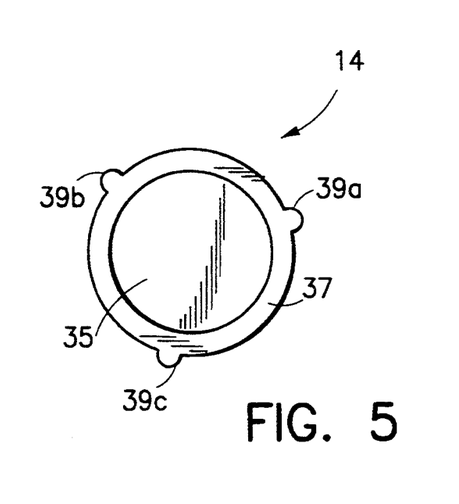
FIG. 5 is an enlarged end view of the valve member looking in the direction 5—5 as indicated in FIG. 1.

Details of the integral valve member 14 are shown in FIGS. 1, 4, and 5. The valve member 14 includes a stem 32 having a diametrical slot 33 at one end. The other end of the stem 32 flares to form a frustroconical sealing surface 36. A valve member base 37 is provided on the other side of the sealing surface 36. The base 37 has an axial bore 35 rendering it hollow. The outer surface of the valve member base 37 is provided with three equidistant longitudinal ribs 39a–39c which are described in further detail below. The valve member stem 32 is sized to fit within the interior 23 of female luer 22 and the sealing surface 36 is sized to abut and sealingly engage the annular ring 27 inside the first cylindrical member 12. At least the base 37 of the valve member is resilient. The integral valve member is preferably molded from silicon, although other materials such as polyurethane would suffice, and the valve member 14 is available as part number V24700 End Valve from Halkey-Roberts Corporation, St. Petersburg, Fla.

Figure 6:
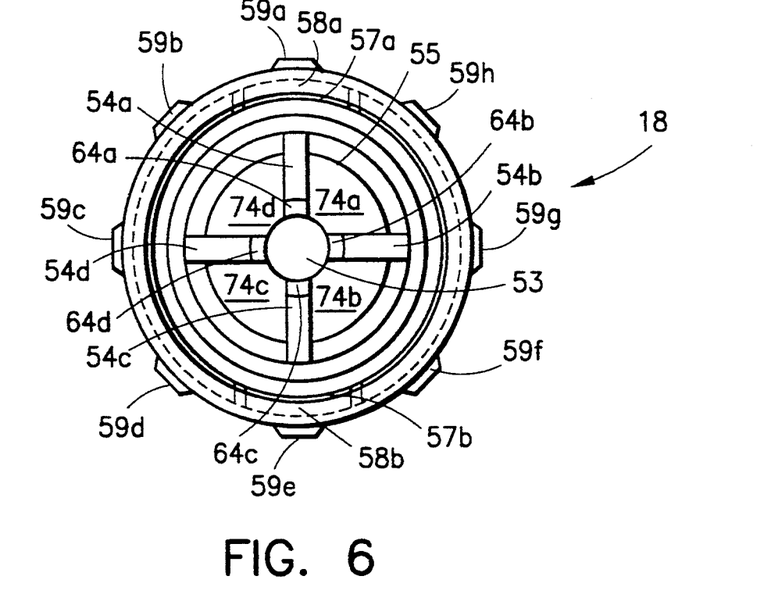
FIG. 6 is an enlarged end view of the second cylindrical member looking in the direction 6—6 as indicated in FIG. 1.
Figure 7:
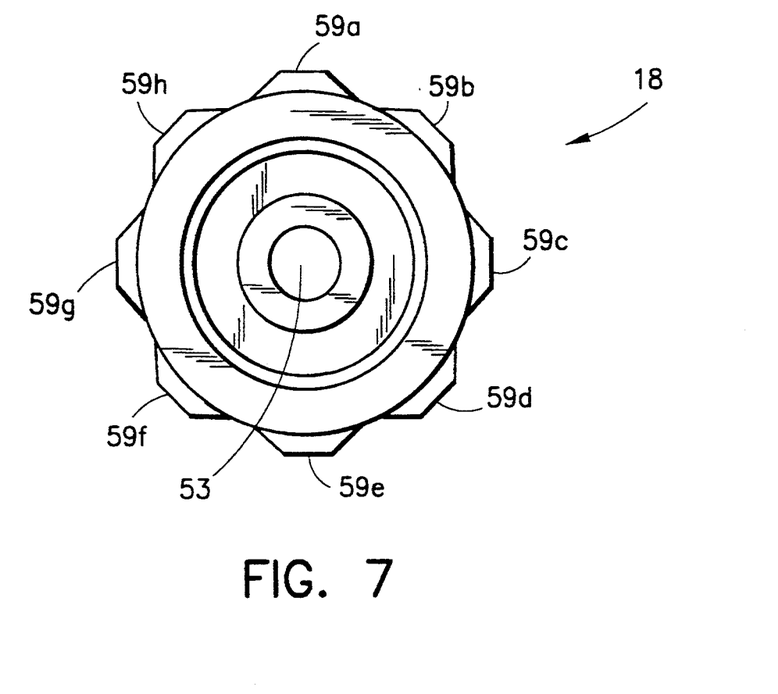
FIG. 7 is an enlarged end view of the male luer connector looking in the direction 7—7 as indicated in FIG. 1.
Figure 8:
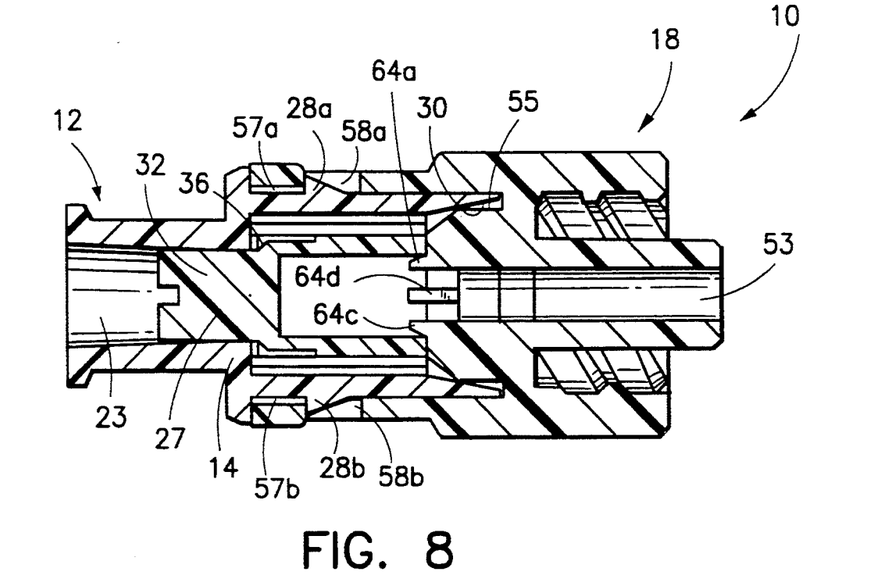
FIG. 8 is a longitudinal cross-sectional view of the embodiment of FIG. 1 assembled with the valve in the normally closed position.
Figure 9:
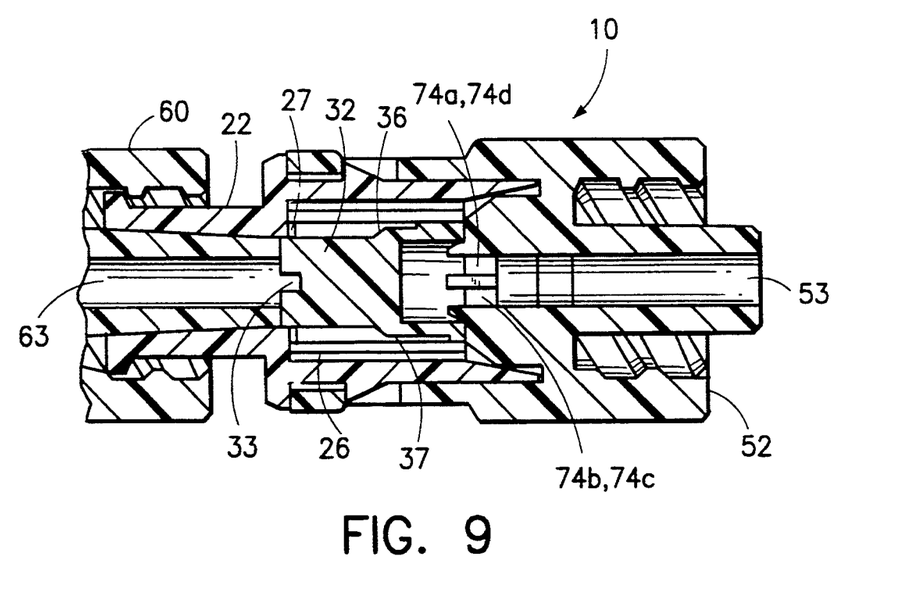
FIG. 9 is a view similar to FIG. 8 with a male luer coupled to the female luer connector engaging the valve member and holding it in the open position.
Figure 10:
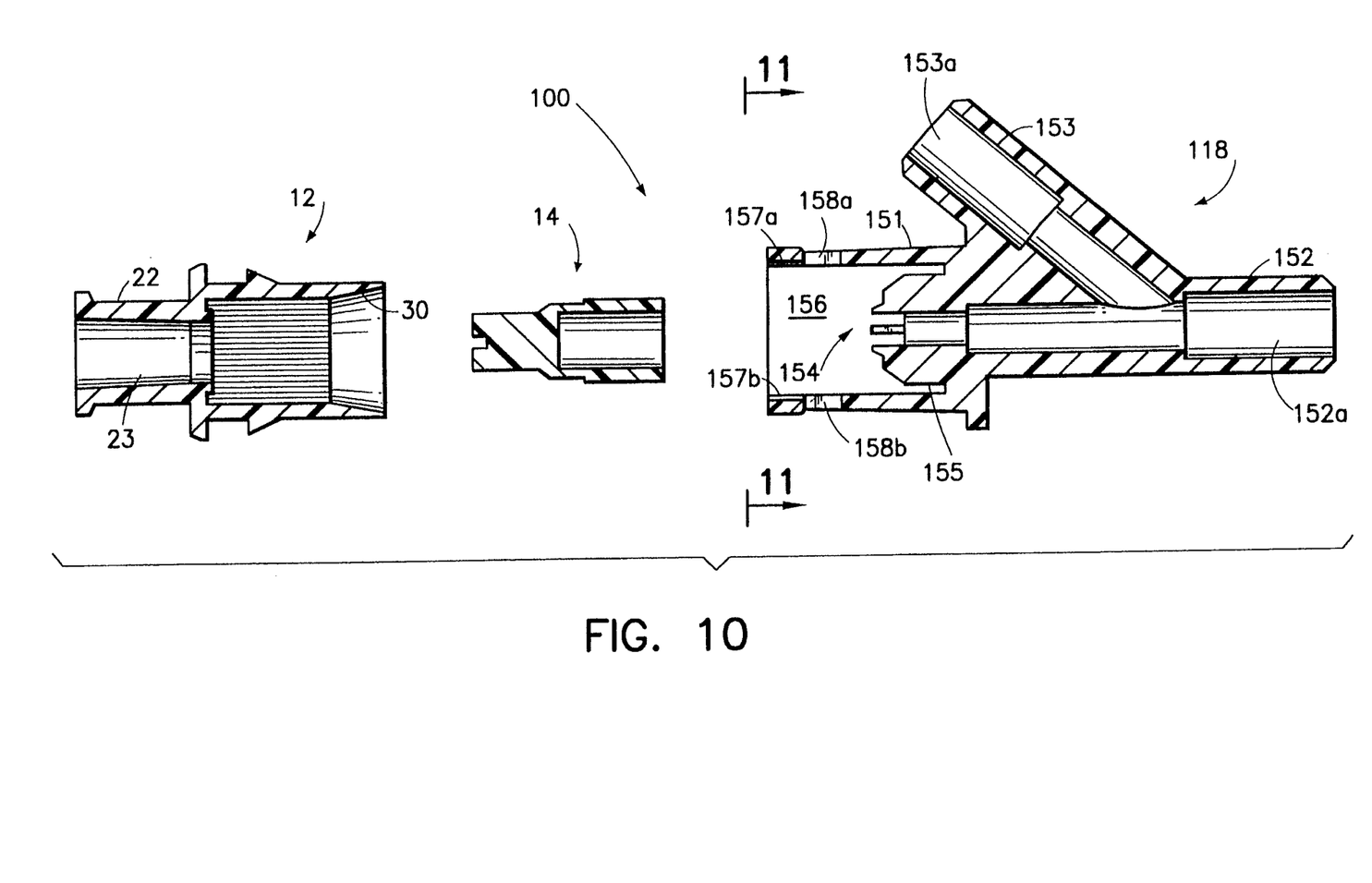
FIG. 10 is an exploded longitudinal cross-sectional view of a second embodiment of the invention.

The second cylindrical member 18 is shown in detail in FIGS. 1, 6, and 7. The second cylindrical member 18 is preferably provided with a male luer connector 52 at one end and an open ended cylinder 51 at the other end. The male luer connector 52 has an interior fluid path 53 which terminates in a valve member seat 54 surrounded by a sealing cylinder 55 inside the interior space 56 of the open ended cylinder 51. The interior space 56 is sized to receive the cylinder portion 25 of the first cylindrical member 12 and the sealing cylinder 55 is sized to fit snugly inside the flared portion 30 of the cylinder 25 as shown in greater detail in FIGS. 8 and 9. Two diametrically opposed longitudinal grooves 57a, 57b are provided on the interior surface of the open ended cylinder 51 for guiding the radially extending ramped protrusions 28a, 28b on the exterior surface of the cylinder portion 25 of the first cylindrical member 12 during assembly as described more fully below. The longitudinal grooves 57a, 57b terminate in radial openings 58a, 58b for receiving and locking the protrusions 28a, 28b as described in detail below. The exterior surface 59 of the male luer connector 52 is provided with a plurality of longitudinally extending radially raised portions 59a–59h which act as a finger gripping surface when the assembly is twisted into connection with another fluid connector (not shown). The valve member seat 54 is composed of four equidistant radial vanes 54a–54d which taper inward from the sealing cylinder 55 and terminate in notched tips 64a–64d as seen best in FIGS. 1 and 6. Spaces 74a–74d between the vanes 54a–54d provide a fluid passage from the interior space 56 of the cylinder 51 to the fluid path 53 of the luer connector 52. As described in more detail below, the tips 64a–64d of the vanes 54a–54d are dimensioned to enter the axial bore 35 in the valve member base 37 as shown in FIGS. 8 and 9. The second cylindrical member is preferably made of clear molded polycarbonate, polystyrene, ABS, or styrene. Thus, the Durometer of the second cylindrical member is greater than the Durometer of the first cylindrical member. This aids in providing a fluid-tight seal between the members when they are assembled.

Assembly of the quick-connect/disconnect device 10 is described with reference to FIGS. 1, S, and 9. The valve stem 32 of the valve member 14 is inserted into the interior space 26 of the cylindrical portion 25 of the first cylindrical member 12 so that it enters the fluid path 23 of the female luer 22 and the sealing surface 36 rests against the annular ring 27. The cylinder portion 25 of the first cylindrical member 12 is then inserted into the open ended cylinder 51 of the second cylindrical member 18 so that the ramped protrusions 28a, 28b align with the longitudinal grooves 57a, 57b. The first cylindrical member 12 and the second cylindrical member 18 are pressed together until the ramped protrusions 28a, 28b enter the radial openings 58a, 58b. In this regard, it will be appreciated that the cylindrical portion 25 and/or the open ended cylinder 51 are provided with sufficient resiliency so that the ramped protrusions 28a, 28b are biased radially inward as they are guided by the longitudinal grooves 57a, 57b and spring radially outward into the radial openings 58a, 58b. Further, it will be appreciated that the protrusions 28a, 28b are ramped in the direction to facilitate assembly and to impede or prevent disassembly. In the assembled state, as shown in FIGS. 8 and 9, the cylindrical portion 25 fully occupies the open ended cylinder 51 with the valve member 14 occupying the interior space 26 of the cylindrical portion 25. The hollow valve member base 37 is supported by the vanes 54a–54d whose notched tips 64a–64d enter the axial bore 35 in the base 37 to center the valve member 14. The distance between the sealing surface 36 of the valve member 14 and the end of the valve member base 37 is slightly larger than the distance between the vanes 54a–54d and the annular ring 27 so that the resilient valve member base 37 biases the valve member 14 to the closed position as shown in FIG. 8 where the valve stem 32 resides in the fluid path 23 of the female luer 22 and the sealing surface 36 abuts the annular ring 27. The flared interior portion 30 of the first cylindrical member 12 surrounds and abuts the sealing cylinder 55 in the second cylindrical portion 18 providing a fluid tight coupling. As mentioned above, the difference in the Durometer of the two cylindrical members aids in providing the fluid tight seal around the sealing cylinder 55. In normal operation, the male luer connector 52 is connected to a female luer connector (not shown) of an IV administration device.

As seen in FIG. 9, when a male luer 60 (shown in a broken segment) is coupled to the female luer connector 22, the stem 32 of the valve member 14 is pressed inward and thereby compresses the resilient valve base 37 against the vanes 54a–54d. In this position, the sealing surface 36 of the valve 14 is moved away from the annular ring 27 in the cylindrical portion 25 of the first cylindrical member 12, and the diametrical slot 33 in the valve stem 32 is open to the interior space 26 of the cylindrical portion 25. A fluid path is thereby established from the interior 63 of luer 60 through the diametrical slot 33 of the valve stem 32, through the interior space 26, around the valve member base 37, through the spaces 74a–74d between vanes 54a–54d and into the fluid path 53 of luer 52. It will be appreciated that the fluid path is bidirectional and that fluid can flow from luer 52 to luer 60 as easily as from luer 60 to luer 52. When the resilient base 37 is compressed, it may buckle outward tending to obstruct the annular space between the valve base and the cylinder 25. In this event, the longitudinal ribs 39a–39c on the valve member base and the longitudinal ribs 29 on the interior of the cylinder 25 help prevent obstruction of the annular space while at the same time, helping to center the valve member 14 within the cylinder 25. It should be appreciated that the longitudinal ribs 29 and 39a–39c should be dimensioned such that ribs 39a–39c can not interleave with ribs 29 and obstruct the passage of fluid.

A second embodiment 100 of the invention is shown in FIGS. 10–13. In this embodiment, the second cylindrical member with male luer is replaced by a Y-site adapter 118. The first cylindrical member 12 and the valve member 14 are the same as in the first embodiment. The Y-site adapter has an open ended cylinder 151, which is substantially the same as the open ended cylinder 51 of the first embodiment, for assembling with the valve body 14 and first cylindrical member 12. The Y-site adapter has two fluid connectors 152 and 153 which define fluid paths 152a and 153a, and a valve member seat 154 with a sealing cylinder 155 inside the interior space 156 of the open ended cylinder 151. The valve member seat 154 and sealing cylinder 155 engage the valve member 14 and first cylindrical member 12 in the same manner as in the first embodiment and as shown in greater detail in FIGS. 12 and 13. The interior space 156 is sized to receive the cylindrical portion 25 of the first cylindrical member 12. Two longitudinal grooves 157a, 157b are provided on the interior surface of the open ended cylinder 151 for guiding the radially extending ramped protrusions 28a, 28b on the exterior surface of the insertable cylindrical portion 25 of the first cylindrical member 12 during assembly as described more fully below. The longitudinal grooves 157a, 157b terminate in radial openings 158a, 158b for locking reception of the protrusions 28a, 28b as described above with respect to the first embodiment. Assembly and operation of the second embodiment 100 is substantially the same as with the first embodiment 10 except for the connections to the fluid paths 152, 153. Typically, the fluid path connector 152 will be coupled to an intravenous tube and the fluid path connector 153 will be coupled to a source of IV fluid. The female luer 22 on the assembled device (FIGS. 12 and 13) will be used for temporarily coupling a supplementary IV fluid source as needed. It will be appreciated that, if desired, the fluid path connector 153 could be manufactured in the same manner as the cylinder 151 and could be arranged to include another cylindrical member 12 and valve member 14. Likewise, fluid path connector 152 could be provided as a male luer slip or lock, or could be provided according to any other desired standard configuration.

Figures 11, 12, 13:
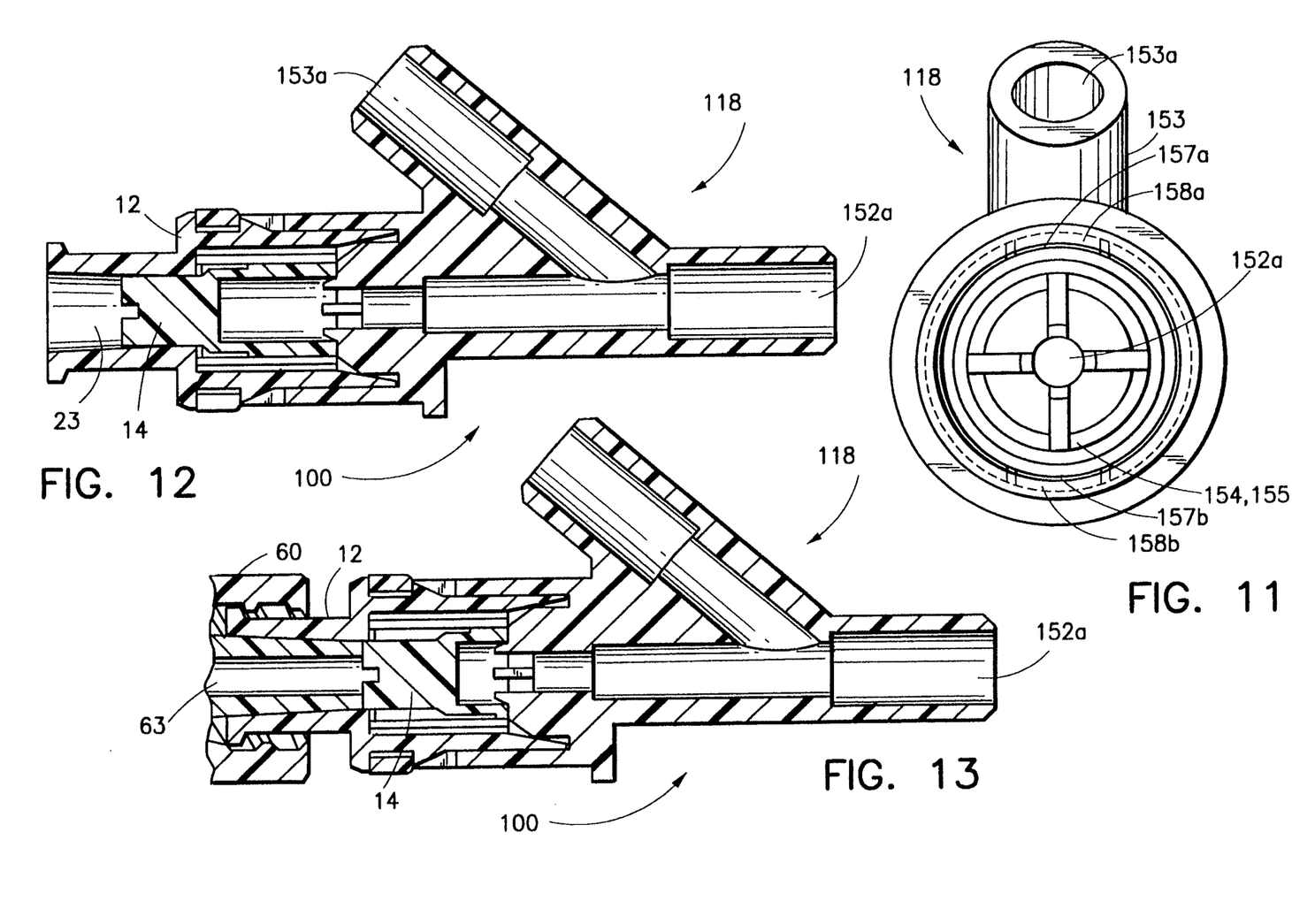
FIG. 11 is an end view of the Y-site adapter looking in the direction 11—11 as indicated in FIG. 10.
FIG. 12 is a longitudinal cross-sectional view of the embodiment of FIG. 10 assembled with the valve in the normally closed position.
FIG. 13 is a view similar to FIG. 12 with a male luer coupled to the female luer connector engaging the valve member and holding it in the open position.

FIGS. 12 and 13 show the assembled second embodiment 100 in the normally closed position and in an open position, respectively. Assembly and operation of the second embodiment 100 is substantially identical with that described above with respect to the first embodiment 10.

Figure 14A:
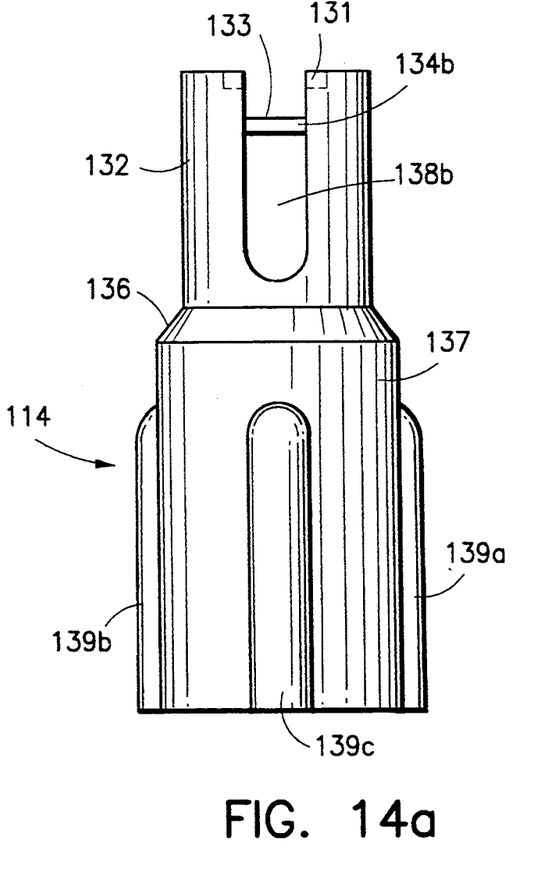
FIG. 14a is an enlarged side elevation view of an alternate valve member of the invention.
Figure 14B:
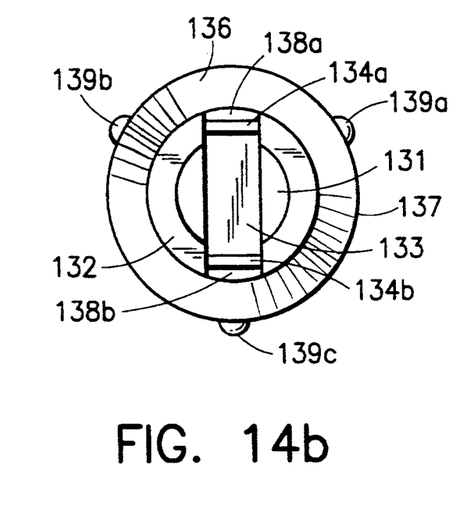
Figure 14C:
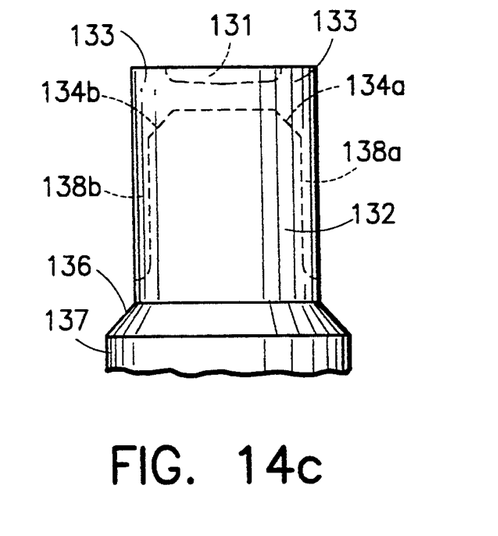

Turning to FIGS. 14a–14c, a preferred embodiment of the integral valve member which is used in conjunction with the coupling cylindrical members 12 and 18 is seen. Valve member 114 is similar to valve member 14 of FIGS. 1, 4, and 5, (and corresponding parts are provided with corresponding numbers one hundred apart) except that valve member 114 is provided with a recessed circular area 131 around the slot 133, chamfered edge sections 134a, 134b of the slot 133, and longitudinal grooves 138a, 138b which run at least partially down the sides of the stem portion 132 of the valve. For structural reasons, the recessed circular area 131 is not as deep as the slot. However, it is preferably sized to have an outer diameter substantially equal to the inner diameter of a standard male luer, so that fluid flowing from the male luer will flow more easily from the recessed area 131 into the slot 133. With the chamfered edge sections 134a, 134b, and the longitudinal grooves 138a, 138b, fluid injected into the slot 133 will disperse radially to the sides of the stem, and axially down the longitudinal grooves 138a, 138b. Thus, when the valve member 114 is compressed by the male luer, it is not necessary that the slot 133 be pushed until it is open to the interior space 26 of the cylindrical portion 25 of the first cylindrical member 12. Rather, all that is required is that the longitudinal grooves 138a, 138b extend into the interior space 26. It will be appreciated that portions of the valve member 114 which are numbered 136, 137, and 139a–139c are substantially identical to portions 36, 37, and 39a–39c described above with reference to valve member 14.

There have been described and illustrated herein a quick-connect/disconnect device for an IV administration line system. While particular embodiments of the invention have been described, it is not intended that the invention be limited thereby, as it is intended that the invention be as broad in scope as the art will allow. Thus, it will be appreciated by those skilled in the art that the term "IV fluid" is intended to be understood in a broad sense to include blood or blood products, and the term "administration" is used in its broad sense to include the dispensing or collection of the "IV fluid". Further, while the connector was illustrated as preferably having a female luer lock on one end, and a male luer lock on the other end, it will be appreciated that, although not preferred, simple luer slips could be utilized in lieu of luer locks. It will also be understood that while one end of the connector must be a female coupling, it is not necessary that the other end of the connector be a male coupling. Moreover, while the assembly has been shown as having two cylindrical portions, one of which fits inside the other, it will be appreciated that either cylindrical portion could extend around the other provided that a cylindrical space is established for the biased valve member. Also, while the valve member has been disclosed as having certain stem, sealing surface, and base configurations, it will be appreciated that other configurations could be used to obtain substantially the same results in substantially the same manner. In addition, while the coupling of the first cylindrical and second cylindrical members is disclosed as a press- and snap-fit with ramped radial protrusions entering radial bores, it will be understood that other types of coupling such as screw coupling, solvent bonding, or sonic welding could be used as well, particularly where both members are of similar materials. Moreover, while the valve member seat has been disclosed as having four radial vanes, it will be understood with the benefit of the instant disclosure that the essence of the valve member seat is to provide a stable support for the valve member base while also providing a fluid path into the male luer. Other types of valve member seats having these features could be substituted without departing from the spirit of the invention. Therefore, it will be appreciated by those skilled in the art that yet other modifications could be made to the provided invention without deviating from its spirit and scope as so claimed.

I claim:

1. A fluid line connection assembly for coupling to and uncoupling from a first fluid pathway which terminates in a first male luer, the fluid line connection assembly comprising:

a) a first coupling member having a first female luer at a first end of said first coupling member and an open first cylindrical chamber at a second end of said first coupling member in fluid communication with said first female luer, said first coupling member having first coupling means, said first cylindrical chamber having a flared inner surface portion;

b) a valve member having a stem, an integral resilient base, and a sealing surface between said stem and said resilient base, said valve member disposed in said first coupling member with said stem extending into said first female luer; and c) a second coupling member having an open second cylindrical chamber, a first fluid coupling member in fluid communication with one of said first cylindrical chamber and said second cylindrical chamber, a second coupling means for mating with said first coupling means, and a valve member support, said second cylindrical chamber having a sealing cylinder portion between said valve member support and said first fluid coupling member; said second coupling member being coupled to said first coupling member when said first coupling means and said second coupling means are mated, with said valve member support supporting said integral resilient base of said valve member such that said sealing surface of said valve member is biased against said first female luer thereby blocking fluid communication between said female luer and said first cylindrical chamber, and with said flared inner surface portion embracing said sealing cylinder portion and forming a fluid-tight seal therebetween, wherein upon coupling the first male luer to said first female luer, the first male luer engages said stem and moves said valve member compressing said resilient base to move said sealing surface away from said female luer, thereby opening fluid communication between said female luer and said first cylindrical chamber, and upon uncoupling the first male luer from said first female luer, the first male luer disengages said stem and said resilient base moves said valve member towards said female luer such that said sealing surface contacts said female luer and blocks fluid communication between said female luer and said first cylindrical chamber.

2. A fluid line connection assembly according to claim 1, wherein:
said sealing surface of said valve member is frustroconical.

3. A fluid line connection assembly according to claim 1, wherein:
said first fluid coupling member comprises a second male luer.

4. A fluid line connection assembly according to claim 1, wherein:
said first cylindrical chamber is provided with a longitudinally ribbed inner surface portion.

5. A fluid line connection assembly according to claim 1, wherein:
said integral resilient base is provided with a plurality of longitudinal exterior ribs.

6. A fluid line connection assembly according to claim 1, wherein:
said first cylindrical chamber has a larger inner diameter than an inner diameter of said female luer, and an intersection of said female luer and said first cylindrical chamber forms a seat on which said sealing surface seals.

7. A fluid line connection assembly according to claim 1, wherein:
one of said first and second coupling means includes a pair of ramped radial protrusions and the other of said first and second coupling means includes a pair of radial recesses for engaging said protrusions thereby locking said first and second coupling members together.

8. A fluid line connection assembly according to claim 1, wherein:
said second coupling member further includes a second fluid coupling member angled relative to said first fluid coupling member, with a fluid passage extending through said second fluid coupling member, said fluid passage being in fluid communication with said first fluid coupling member.

9. A fluid line connection assembly according to claim 1, wherein:
said valve member support includes a fluid passage in fluid communication with said first fluid coupling member.

10. A fluid line connection assembly according to claim 9, wherein:
said valve member support comprises a plurality of radial vanes and said fluid passage comprises a space between said radial vanes.

11. A fluid line connection assembly according to claim 10, wherein:
said radial vanes taper inward toward said integral resilient base and terminate with notched tips, and said integral resilient base is provided with an axial bore which receives said notched tips.

12. A fluid line connection assembly according to claim 1, wherein:
said valve member stem is provided with a fluid channel, and
when said sealing surface is moved away from said first female luer, fluid communication between said first female luer and said first cylindrical chamber is through said fluid channel.

13. A fluid line connection assembly according to claim 12, wherein:
said fluid channel includes a diametrical slot in said valve member stem.

14. A fluid line connection assembly according to claim 13, wherein:
said valve member stem has side walls, and said fluid channel further includes longitudinal grooves in said side walls of said valve member with said longitudinal grooves being in fluid communication with said diametrical slot.

15. A fluid line connection assembly according to claim 14, wherein:
said valve member stem has a top surface interrupted by said diametrical slot, said diametrical slot having a first depth, and said top surface further having a recessed circular area of a second depth which is less deep than said first depth.

16. A fluid line connection assembly according to claim 14, wherein:
said valve member support includes a fluid passage in fluid communication with said first fluid coupling member, and
said valve member support comprises a plurality of radial vanes and said fluid passage comprises a space between said radial vanes.

17. A fluid line connection assembly according to claim 16, wherein:
said radial vanes taper inward toward said integral resilient base and terminate with notched tips, and said integral resilient base is provided with an axial bore which receives said notched tips.

18. A fluid line connection assembly for coupling to and uncoupling from a first fluid pathway which terminates in a first male luer, the fluid line connection assembly comprising:
a) a first coupling member having a first female luer at a first end of said first coupling member and an open first cylindrical chamber at a second end of said first coupling member in fluid communication with said first female luer, said first coupling member having first coupling means;
b) a valve member having a stem, an integral resilient base, and a sealing surface between said stem and said resilient base, said valve member disposed in said first coupling member with said stem extending into said first female luer; and
c) a second coupling member having an open second cylindrical chamber, a first fluid coupling member in fluid communication with one of said first cylindrical chamber and said second cylindrical chamber, a second coupling means for mating with said first coupling means, and a valve member support, said second coupling member being coupled to said first coupling member when said first coupling means and said second coupling means are mated, with said valve member support supporting said integral resilient base of said valve member such that said sealing surface of said valve member is biased against said first female luer thereby blocking fluid communication between said female luer and said first cylindrical chamber, wherein:
one of said first and second coupling means includes a pair of ramped radial protrusions and the other of said first and second coupling means includes a pair of radial recesses for engaging said protrusions thereby locking said first and second coupling members together.

* * * * *